United States Patent [19]

Kirkpatrick et al.

[11] Patent Number: 4,983,268

[45] Date of Patent: Jan. 8, 1991

[54] HIGH GEL STRENGTH LOW ELECTROENDOSMOSIS AGAROSE

[75] Inventors: Francis H. Kirkpatrick, Owls Head; Kenneth Guiseley, Union; Richard Provonchee, Camden, all of Me.; Samuel Nochumson, Randolph, N.J.

[73] Assignee: FMC Corporation, Philadelphia, Pa.

[21] Appl. No.: 389,141

[22] Filed: Aug. 3, 1989

[51] Int. Cl.$^5$ .................... C07K 1/14; C07K 3/14; B01D 57/02

[52] U.S. Cl. .................... 204/182.8; 204/299 R; 252/315.3; 106/205; 536/3; 536/114; 536/127

[58] Field of Search .................... 204/182.8, 299 R; 252/315.3; 536/3, 114, 127; 106/205

[56] References Cited

U.S. PATENT DOCUMENTS 4,290,911  9/1981  Cook et al. .................... 252/315.3

OTHER PUBLICATIONS

Bio-Rad, "Price List L", Jan. 1976, p. 172.

Zajic, "Properties and Products of Algae", 1970, pp. 57-60; p. 143.

Primary Examiner—John F. Niebling
Assistant Examiner—David G. Ryser
Attorney, Agent, or Firm—Patrick C. Baker; Mark A. Greenfield

[57] ABSTRACT

Purified agarose suitable for rapid electrophoresis, characterized by a sulfate content of less than 0.2 wt % but greater than zero, a pyruvate content of 0–0.1 wt %, and a nitrogen content of 0–0.02 wt %. Gels prepared from the agarose exhibit a gel strength at 1.0 wt % concentration of at least 1200 g/cm$^2$, substantial absence of DNA binding in 0.07 M or less tris acetate buffer, and an electroendosmosis (EEO) at 1.0 wt % concentration of 0.05 or less. Agaroses are purified to provide the low EEO material by dissolving agarose or alkali-modified agar in an aqueous medium buffered at a pH of 6.0 to 8.0 and containing no more than 2.0 nM salt as chloride, and precipitating the agarose by contact with a lower alkanol.

23 Claims, No Drawings

HIGH GEL STRENGTH LOW ELECTROENDOSMOSIS AGAROSE

BACKGROUND OF THE INVENTION

This invention relates to agarose compositions having improved properties, particularly low electroendosmosis (EEO), for use in electrophoresis and other diffusive procedures or interactions. The invention further relates to processes for purifying agaroses to improve their electrophoretic properties, and to methods of using the agaroses in electrophoresis and other applications.

The rapid expansion of interest in the purification and separation of biomolecules such as proteins and nucleic acids, the mapping of genes, and DNA sequencing, has placed increased demands on agaroses as separation media. Agaroses have been prepared commercially by the polyethylene glycol method of Polson (U.S. Pat. No. 3,335,127), the aluminum hydroxide adsorption method of Barteling, *Clin. Chem.* 15, 1002–1005 (1969), and the quaternary ammonium salt/sulfated polysaccharide method of Blethen (U.S. Pat. No. 3,281,409). In all of these methods the larger, least-charged agarose molecules are separated from the more highly charged agaropectin molecules.

Although agaroses prepared by these methods remain satisfactory for many electrophoretic, immunodiffusion and chromatographic applications, agaroses are now required which not only have high gel strength (to allow use at low concentrations - the larger pores permit separation of larger molecules), but also allow faster, more reliable and precise separations, and detection of minute quantities of material.

Various purification techniques have been developed in efforts to produce improved agaroses, beginning with the ion exchange work of Zabin (U.S. Pat. No. 3,423,396) and Duckworth and Yaphe (U.S. Pat. No. 3,753,972), and continuing with the work of Laas and co-workers (J. Chromatogr 60 (1971), 167–177 and 66 (1972), 3476–355; Anal. Biochem. 72 (1976), 527–532) on alkaline desulphation followed by alcohol precipitation and reduction with lithium aluminum hydride. However, these methods result in material which does not have reliable quality or require expensive and/or unsafe procedures. Exhaustive treatment with alkali will remove much of the sulfate but can also degrade the gel strength of agar and agarose.

For preparation of agaroses for use where low, essentially zero, EEO is important, as in isoelectric focusing, the residual EEO can be suppressed by addition of a gum such as clarified locust bean or guar gum (U.S. Pat. No. 4,290,911 to Cook and Witt) or charge balanced by introduction into the agarose of positively-charged groups (U.S. Pat. No. 4,312,739 to Hansson and Kagedal). When used in electrophoresis, however, these media tend to bind (immobilize) biomolecules such as DNA because of the added materials or groups. The media also have lower gel strength and the modifications adversely affect their gelling and melting temperatures.

Lai, Birren and colleagues, in studying various forms of pulsed field gel electrophoresis, determined that DNA moves fastest in gels prepared from agaroses of low EEO, thus relating speed of separation to EEO (BioTechniques 7, No. 1 (1989), 34–42, at 39). This relationship thus has become a partial measure of usefulness of agaroses for modern electrophoretic processes.

SUMMARY OF THE INVENTION

A class of agaroses has now been found that satisfies the need for electrophoretic processing media which facilitate fast running time (of the order of 50% or more reduction in time), detection of extremely small amounts of material, clean and reliable separations but which also exhibit high gel strength. The combination of these benefits qualifies these agaroses as eminently useful in the electrophoretic purification and separation of biomolecules of a wide range of sizes.

In one aspect of the invention, a dry solid composition is provided which is capable of forming an aqueous gel useful for rapid electrophoresis. The agarose composition consists essentially of a purified agarose having a sulfate content of less than 0.2 wt % but greater than zero, a pyruvate content of 0–0.1 wt %, and a Kjeldahl nitrogen content of 0–0.04 wt %. The gels formed from the agarose exhibit a gel strength of at least 1200 g/cm$^2$ (1.0 wt % concentration), substantial absence of DNA binding in 0.07 M or less tris acetate buffer, and an EEO at 1.0 wt % agarose concentration of 0.05 or less.

In another aspect of the invention, various methods are provided for preparation of the low EEO agaroses by purification of precursor agaroses, including ion exchange, fractionation with low molecular weight polyol, chromatographic separation on a modified silica substrate, fractionation with a lower ($C_1$–$C_4$) alcohol under controlled salt conditions, and other techniques, including combinations of any of the methods. The invention further includes the agaroses produced by the methods of purification.

In still another aspect of the invention, electrophoretic methods of separation and purification are provided, wherein the separation/purification media are the improved, fast running agaroses described above.

DETAILED DESCRIPTION

Electroendosmosis (EEO) may be described as the drift of a fluid through an aqueous gel towards an electrode during electrophoresis. The drift occurs when electrically neutral, or nearly neutral, molecules are present in a sample to be electrophoresed, and the gel medium carries a charge. When agarose is the medium, anionic residues such as ester sulfate and pyruvate groups are present and impart a net negative charge to the gel. Although the gel itself can't move anodally, the water sphere around it is pulled or distorted toward the cathode by hydrated cations associated with the bound anions. As a result, neutral molecules in the sample are gradually pulled towards the cathode with the water.

EEO is expressed numerically as relative mobility ($-m_r$) and is measured by preparing a 1% by weight solution of the agarose in 0.05 M, pH 8.6, barbital buffer. Three milliters of the solution is poured on a clean microscope slide and allowed to gel at room temperature. Using a squared off No. 13 needle attached to a hypodermic syringe, a single hole is aspirated from the center of the gel. A standard test solution is prepared which consists of 10 mg/ml Dextran 500 (Pharmacia) and 2 mg/ml crystalline (4x) human albumin in 0.05 M, pH 8.6, barbital buffer. Using a small bore dropper, sufficient solution is added to nearly fill the aspirated hole. These slides are then placed in position for electrophoresis using paper wicks. A potential of 10 volts/cm (75 volts) is applied using constant voltage settings.

Electrophoresis is continued for three hours, then the slides removed. Visualization is accomplished in two stages. The slides are first placed in denatured (3A) ethanol for 15 minutes after which time the position of the dextran can be measured with respect to the origin (OD=distance from origin to dextran, center to center). After measuring, the slides are transferred to protein staining solution prepared from 0.5 g amido black in 50 ml glacial acetic acid, then made up to 500 ml with ethanol. After 15 minutes the slides are washed in a 1:1 acetic acid (5%):ethanol solution to remove excess stain. An hour is sufficient although the albumin position can usually be determined after 15 minutes. The distance from the center of the spot to the center of the origin is measured (OA=distance from origin to albumin). The degree of electroendosmosis ($-m_r$) can be calculated using the equation:

$$-m_r = (OD/OA + OD)$$

The gel strengths (also known as "breaking strengths") referred to herein can be measured by using the procedure and apparatus described in Foster et al. U.S. Pat. No. 3,342,612 granted Sept. 19, 1967, the description of which is incorporated herein by reference, and by providing an automatic drive to advance the plunger at a constant rate of 16.83 cm/min. Gelation is accompliShed for purpose of the test by cooling the solution in a water bath at 10° C. for 2 hours. The gel is then removed from the water bath and gel strength measured, using a circular plunger having an area of 1 cm$^2$.

The substantial absence of DNA binding that characterizes the agaroses of the invention is determinable in several ways but generally is characterized by substantially no measurable retardation of mobility of 2.03 kb DNA at 22° C. and a voltage gradient of 4 V/cm in a 1.0 wt % agarose gel buffered with 0.01 M or less tris acetate buffer. A preferred tris acetate buffer concentration for the test is 0.062 M. "Tris acetate buffer" is a mixture of tris(hydroxymethyl)aminomethane, sodium acetate and sodium EDTA [ethylene diamine tetra acetic acid (sodium salt)] adjusted to pH 7.8, typically at concentrations of 0.04 M, 0.02 M and 0.002 M, respectively.

Agar sources suitable for preparing the agaroses of the invention preferably are those low in sulfate and pyruvate (carboxylate) contents so that less processing is required to reduce the sulfate and pyruvate to the requisite levels. Accordingly, the preferred agars are those derived from Gelidium, Gracilaria and Pterocladia algal species, or any mixtures thereof, although others may be useful if processing to the requisite sulfate and pyruvate contents is economical.

The process of the invention may be practiced not only on agar but also on alkali-treated agar, on agaroses unduly high in the properties which define the compositions of the invention.

While the compositions of the invention include those defined by the ranges of properties set forth in the Summary statement above, the preferred compositions are those wherein the sulfate content is 0–0.15 wt %, the pyruvate content is 0–0.1 wt %, the Kjeldahl nitrogen content is 0.001–0.02 wt %, the gel strength is at least 1600 g/cm$^2$, and the composition will exhibit an EEO at 1.0 wt % agarose concentration of 0.04 or less. Furthermore, the agaroses will contain substantially no modifications, except for reduced aldehyde residues incidental to sodium borohydride treatment during processing from algal species. Preferably, the purified agarose will be free of ash residues although up to about 0.5 wt % ash (more preferably, up to 0.3 wt %) is tolerable.

The compositions comprise the agaroses either in the dry state, in finely divided particulate or other useful form, or as aqueous gels containing an electrophoretically effective amount of the agarose in hydrated form, for example, from about 0.03 to about 10 wt % of agarose (dry) based on total gel weight.

Because the parameters of sulfate, pyruvate and nitrogen content, gel strength, absence of DNA binding and EEO set forth above have been found to be reliable in predicting agaroses providing improved running times illustrated in the examples, a variety of purification processes are applicable to obtain the agaroses. Thus anion exchange resins can be used, with care taken to avoid contamination of the product with the resin. Suitable ion exchange resin methods are described in the literature and in U.S. Pat. Nos. 3,423,396 to Zabin and 3,753,972 to Duckworth and Yaphe. Other methods include fractionation with low molecular weight polyol as described in the European Patent Application 304024 of R.B. Provenchee published Feb. 22. 1989, separation on a modified silica support described in U.S. Pat. Nos. 3,862,030 to Goldberg and 4,689,302 to Goldberg and Chen, fractionation with alcohol under controlled salt concentration conditions, and combinations of the methods. The foregoing publications, patents and patent applications are incorporated herein by reference.

In the controlled salt/alcohol fractionation method, the starting agarose is slurried into distilled water, and repeatedly filtered and resuspended until conductivity measurements indicate that the salt content has been reduced to as low a level as economically feasible, for example to a level corresponding to about 3 mM or less as NaCl. The resulting suspension is then boiled to dissolve the agarose, cooled to about 70–75° C., precipitated with a lower ($C_1$–$C_4$) alcohol such as isopropyl alcohol (heated to about 40° C.), and the precipitate rinsed, dried and ground (if desired). The amount of alcohol and other conditions of the precipitation (temperature, pH, method of mixing the agarose and alcohol) will control the degree of ionic strength and physical character of the resulting agarose, and may be varied accordingly. For example, below pH 6.5 the agarose generally precipitates as a fine mass; above pH 7.5 it tends to become ropey and difficult to handle. Accordingly, a pH of about 6–8 is preferred for the precipitation step, more preferably about 7.2. Furthermore, higher salt content can be tolerated if the agarose is precipitated by adding alcohol to the agarose sol (aqueous phase), rather than the reverse. Generally, however, the salt content of the aqueous phase should not exceed 2.0 mM as NaCl. A preferred salt concentration is 0.003 to 0.8 mM, more preferably not over 0.4 mM, on the same basis.

The product agarose can be used in any of the many electrophoretic or diffusion procedures for which agarose media are conventionally used, and in accordance with well known protocols. For example, in addition to electrophoresis, the agaroses are useful for isoelectric focusing, chromatographic separations, and other processes for separating, assaying, supporting, transforming (culturing, cleaning, cloning, etc.) or treating biological materials.

The following examples are intended as further illustration of the invention but not as limitations on the scope thereof.

EXAMPLE 1

Twenty grams of agarose derived from Gelidium seaweed (SeaKem ® LE agarose, FMC BioProducts) was stirred in one liter of distilled water at room temperature. After 15 minutes, the conductivity of the slurry was measured and found to be 50.0 μmhos, corresponding to 0.427 mM, or about 0.025 g of sodium chloride, based on a standard curve prepared in advance. The agarose was separated from the liquid by filtration through Whatman No. 54 paper on a Buechner funnel, producing a wet cake of 86.3 g. This was resuspended in 933.7 mL distilled water and stirred as before. The equilibrium value of the conductivity was 34 μmhos, corresponding to a sodium chloride concentration of 3 μM, or about 0.18 mg/L.

The agarose was again filtered off, then resuspended in water to a total weight of 1000 g, and dissolved by boiling, thus forming a 2% solution. It was cooled to 74° C. and mixed with two liters of azeotropic isopropyl alcohol (IPA) (87.7% by weight IPA) heated to 42° C., by simultaneously pouring both liquids into a third container to maximize uniform mixing. The mixture was cooled to 32° C. and the resulting precipitate separated from the cloudy supernatant liquid by pouring the entire mixture through a 120-mesh screen. The precipitate was rinsed twice on the screen with a stream of 60% IPA from a squeeze bottle, then pressed with a rubber spatula, and dried in a circulating air oven at 55° C.

The dried product was ground through a 20-mesh (US) screen in a laboratory grinding mill (Wiley mill), and subsequently analyzed and tested. Pyruvate analysis was by the method of Duckworth and Yaphe (lactate dehydrogenase), Chem. Ind. 747–748 (1970). Gel strength was measured on 1.0 wt % sample. Nitrogen is by the Kjeldahl method. The results, in comparison with the starting (parent) agarose, are given in Table 1.

TABLE 1

|  | Parent Agarose | Purified Agarose |
| --- | --- | --- |
| Yield, wt % | — | 53.9 |
| Gel Str., g/cm$_2$ | 1406 | 1814 |
| Ash, wt % | 0.62 | 0.18 |
| Sulfate, wt % | 0.14 | 0.07 |
| EEO ($-m_r$) | 0.11 | 0.05 |
| Nitrogen, wt % | 0.01 | 0.01 |
| Pyruvate, wt % | 0.185 | 0.072 |

In addition, no binding was observed when DNA was electrophoresed in 1.0 wt % of the purified agarose in tris acetate buffer at pH 7.8 under the following conditions:

DNA:
  Hin dIII digest of lambda phage, 172 ng.
Buffer:
  40 mM tris (hydroxymethyl) aminomethane
  20 mM sodium acetate
  2 mM sodium EDTA
Electrophoresis:
  4 volts/cm gradient for 3 hours at 22° C.
Standard for non-binding:
  6th band
  (2.03 kb DNA) is visible when stained with ethidium bromide at 1 mg/L for 20 minutes, and travels at least 5 cm.

EXAMPLE 2

Twenty grams of agarose isolated from Pterocladia agar was slurried in one liter of distilled water and a few drops of dilute sodium hydroxide solution were added to raise the pH to 7.2 The slurry was heated to boiling, then cooled to 54° C. and to it was added two liters of azeotropic isopropyl alcohol also at 54° C. The resulting precipitate was treated as in Example 1 and analyzed. The results, measured as in Example 1, are given in Table 2. The purified agarose, when tested as in Example 1, was non-binding to DNA.

TABLE 2

|  | Parent Agarose | Purified Agarose |
| --- | --- | --- |
| Yield, wt % | — | 44.4 |
| Gel Str., g/cm$_2$ | 1046 | 1420 |
| Ash, wt % | 0.64 | 0.11 |
| Sulfate, wt % | 0.11 | 0.07 |
| EEO ($-m_r$) | 0.10 | 0.04 |
| Nitrogen, wt % | 0.01 | 0.01 |
| Pyruvate, wt % | 0.008 | 0.003 |

EXAMPLE 3 (Comparative)

Example 2 was repeated using a Gelidium agarose having a higher ash content. As Table 3 indicates, the EEO of the recovery agarose did not have the properties defining the agarose of the invention. The data were obtained as in Example 1. ("NA" means not assayed.)

TABLE 3

|  | Parent Agarose | Purified Agarose |
| --- | --- | --- |
| Yield, wt % | — | 37.9 |
| Gel Str., g/cm$_2$ | 1020 | 1500 |
| Ash, wt % | 0.74 | NA |
| Sulfate, wt % | 0.14 | 0.16 |
| EEO ($-m_r$) | 0.13 | 0.07 |
| Nitrogen, wt % | NA | NA |
| Pyruvate, wt % | 0.147 | 0.090 |

EXAMPLE 4

Thirty grams of Gelidium agarose were dispersed in a mixture of 1000 ml of propylene glycol and 50 ml water, and dissolved by heating to 135° C. On cooling, a precipitate formed, which was collected and washed with isopropyl alcohol. The properties of the fractionated agarose, measured as in Example 1, are shown in Table 4. The purified agarose did not bind DNA when tested as in Example 1.

TABLE 4

|  | Parent Agarose | Purified Agarose |
| --- | --- | --- |
| Gel Str., g/cm$^2$ | 1440 | 1680 |
| Ash, wt % | 0.37 | 0.02 |
| Sulfate, wt % | 0.03 | 0.03 |
| EEO ($-m_r$) | 0.10 | 0.04 |
| Nitrogen, wt % | 0.01 | 0.004 |
| Pyruvate, wt % | 0.187 | 0.069 |

EXAMPLE 5

Example 4 was repeated in all essential respects except that Gracilaria agarose was substituted for Gelidium agarose. The properties are given in Table 5. The purified agarose did not bind DNA when tested as in Example 1.

TABLE 5

| | Parent Agarose | Purified Agarose |
|---|---|---|
| Gel Str., g/cm$^2$ | 1034 | 1514 |
| Ash, wt % | 0.52 | 0.20 |
| Sulfate, wt % | 0.13 | 0.10 |
| EEO ($-m_r$) | 0.09 | 0.05 |
| Nitrogen, wt % | 0.013 | 0.007 |
| Pyruvate, wt % | 0.01 | 0.003 |

Agarose was prepared from Gracilaria seaweed by the aluminum hydroxide adsorption method or Barteling [*Clinical Chemistry*, 15, 1002–1005 (1969)] and analyzed as in Example 1. The product had the following properties:

TABLE 6

| Gel Str., g/cm$^2$ | 1340 |
|---|---|
| Sulfate, wt % | 0.12 |
| EEO ($-m_r$) | 0.05 |

Nitrogen and pyruvate analysis were not carried out-nitrogen because nitrogenous substituents were not introduced; pyruvate because Gracilaria agar does not contain pyruvate. The conductivity of the product was found to be 40 μmhos, corresponding to a salt concentration (as NaCl) of 0.336 mM.

We claim:

1. A dry solid composition capable of forming an aqueous gel useful for rapid electrophoresis, said composition consisting essentially of purified agarose characterized by a sulfate content of less than 0.2 wt % but greater than zero, a pyruvate content of 0–0.1 wt %, and a nitrogen content of 0–0.2 wt %, said gels characterized by a gel strength at 1.0 wt % concentration of at least 1200 g/cm$^2$, substantial absence of DNA binding in 0.7 M or less tris acetate buffer, and an electroendosmosis at 1.0 wt % concentration of 0.05 or less.

2. The composition of claim 1 wherein the agarose is derived from Gelidium, Gracilaria or Pterocladia agar, or mixtures of two or more thereof.

3. An aqueous gel comprising a gelled solution in water of the composition of claim 2.

4. The composition of claim 1 wherein the sulfate content is 0.15 wt % or less, the nitrogen content is 0.001–0.02 wt %, and the gel strength is at least 1600 g/cm$^2$.

5. An aqueous gel comprising a gelled solution in water of the composition of claim 4.

6. The composition of claim 1 wherein the electroendosmosis is about 0.04 or less.

7. The composition of claim 1 wherein the absence of DNA binding is characterized by substantially no retardation of mobility of 2.03 kb DNA at 22° C. and a voltage gradient of 4 V/cm in a 1.0 wt % gel buffered with 0.07 M or lower concentration of tris acetate.

8. An aqueous gel comprising a gelled solution in water of the composition of claim 7.

9. The composition of claim 1 wherein the agarose is derived from Gelidium, Gracilaria or Pterocladia agar, or mixtures of two or more thereof, the sulfate content is 0.15 wt % or less, the nitrogen content is 0.001–0.02 wt %, and the gel strength is at least 1600 g/cm$^2$.

10. An aqueous gel comprising a gelled solution in water of the composition of claim 9.

11. The composition of claim 1 in particulate form.

12. An aqueous gel comprising a gelled solution in water of the composition of claim 1.

13. The aqueous gel of claim 12 wherein the composition is present in an amount of from about 0.1 to about 5.0 wt % on total weight of the gel.

14. In a method of electrophoretically separating biological materials in a separation medium, the improvement which comprise employing as the separation medium the aqueous gel of claim 12.

15. A process for purifying an agarose to provide the composition of claim 1, comprising dissolving agarose or alkali-modified agar in an aqueous medium buffered at pH of 6.0 to 8.0 and containing no more than 2.0 mM salt as chloride, and precipitating the agarose by contact with a lower alkanol.

16. The process of claim 15 wherein the lower alkanol is isopropanol.

17. The purified agarose prepared by the process of claim 16.

18. The process of claim 15, wherein the pH is about 7.2 and the salt content is in the range of 0.003 to 0.8 mM.

19. The process of claim 15 wherein the lower alkanol is isopropanol, the pH is about 7.2, and the salt content is in the range of 0.003 to 0.4 mM.

20. The purified agarose prepared by the process of claim 19.

21. The process of claim 15 wherein the alkanol is added to the aqueous medium.

22. The purified agarose prepared by the process of claim 21.

23. The purified agarose prepared by the process of claim 15.

* * * * *

UNITED STATES PATENT AND TRADEMARK OFFICE
CERTIFICATE OF CORRECTION

PATENT NO. : 4,983,268

DATED : January 8, 1991

INVENTOR(S) : Francis H. Kirkpatrick, Kenneth Guiseley, Richard Provonchee, Sameul Nochumson It is certified that error appears in the above-identified patent and that said Letters Patent is hereby corrected as shown below:

Column 3, line 49, the words Gelidium, Gracilaria, and Pterocladia should be underlined. Column 3, line 65, after the word "no" insert --artificially substituted groups or other chemical--. Column 5, line 1, the word Gelidium should be underlined. Column 6, line 1, the word Pterocladia should be underlined. Column 6, line 26, the word Gelidium should be underlined. Column 6, line 44, the word Gelidium should be underlined. Column 6, line 65, the word Gracilaria should be underlined. Column 6, line 66, the word Gelidium should be underlined. Column 7, line 10, please insert --EXAMPLE 6--.

Column 7, line 24, the word Gracilaria should be underlined. Column 7, line 35, the word "gels" should read --gel--. Column 7, line 38, "0.7" should read --0.07. Column 7, line 41, the words Gelidium, Gracilaria, and Pterocladia should be underlined. Column 8, line 11, the words Gelidium, Gracilaria, and Pterocladia should be underlined.

Signed and Sealed this

Twelfth Day of January, 1993

Attest:

DOUGLAS B. COMER

Attesting Officer

Acting Commissioner of Patents and Trademarks